(12) United States Patent
Tryggvason et al.

(10) Patent No.: US 8,617,482 B2
(45) Date of Patent: Dec. 31, 2013

(54) MAINTAINING STERILE CONDITIONS IN A FLUID TRANSPORTATION SYSTEM

(75) Inventors: Ragnar Tryggvason, Löddeköpinge (SE); Mikael Axelsson, Furulund (SE)

(73) Assignee: Gambro Lundia AB, Lund (SE)

( * ) Notice: Subject to any disclaimer, the term of this patent is extended or adjusted under 35 U.S.C. 154(b) by 199 days.

(21) Appl. No.: 12/999,265

(22) PCT Filed: Jun. 15, 2009

(86) PCT No.: PCT/EP2009/057321
§ 371 (c)(1),
(2), (4) Date: Dec. 15, 2010

(87) PCT Pub. No.: WO2009/153224
PCT Pub. Date: Dec. 23, 2009

(65) Prior Publication Data
US 2011/0165020 A1    Jul. 7, 2011

Related U.S. Application Data

(60) Provisional application No. 61/073,051, filed on Jun. 17, 2008.

(30) Foreign Application Priority Data

Jun. 17, 2008    (SE) .................................... 0801414

(51) Int. Cl.
*A61L 2/00* (2006.01)
*A61M 37/00* (2006.01)
*A61M 5/315* (2006.01)
*F16L 55/10* (2006.01)

(52) U.S. Cl.
USPC .............. 422/292; 604/132; 604/236; 138/89

(58) Field of Classification Search
USPC ................... 422/301–302, 28, 292; 128/349, 128/219–220; 222/390; 604/132, 212, 217, 604/236, 280; 251/149.7; 138/89
See application file for complete search history.

(56) References Cited

U.S. PATENT DOCUMENTS 4,432,764 A * 2/1984 Lopez ........................... 604/533
5,205,821 A * 4/1993 Kruger et al. .................... 604/91

(Continued)

FOREIGN PATENT DOCUMENTS

WO   WO 87/00441        1/1987
WO   WO 2004/071557 A1  8/2004

*Primary Examiner* — Monzer Chorbaji
(74) *Attorney, Agent, or Firm* — Finnegan, Henderson, Farabow, Garrett & Dunner LLP

(57) ABSTRACT

A capping device is configured to terminate a connector while disconnected from another connector in a fluid transportation system, e.g., for peritoneal dialysis. The connector comprises an exposed surface portion that is enclosed when the connector is connected to the other connector. The capping device comprises a body defining a chamber with an opening, a liquid-containing disinfectant in the chamber, a sealing element arranged in the opening to form a sealed cavity retaining the disinfectant, and a structure for engaging and guiding the connector towards the body such that a portion of the connector displaces the sealing element into the chamber. The sealed cavity is configured such that a displacement of the sealing element into the chamber actively presses the disinfectant out of the sealed cavity, for disinfecting at least part of the exposed surface portion. The capping device may be manufactured by introducing the liquid-containing disinfectant into the chamber through the opening, and by arranging the sealing element in the opening to form the sealed cavity.

18 Claims, 10 Drawing Sheets

(56) References Cited

U.S. PATENT DOCUMENTS

| | | | |
|---|---|---|---|
| 5,385,546 A * | 1/1995 | Kriesel et al. | 604/85 |
| 6,171,287 B1 * | 1/2001 | Lynn et al. | 604/256 |
| 7,232,419 B2 | 6/2007 | Castellanos | |
| 2003/0144647 A1 | 7/2003 | Miyahara | |
| 2006/0189961 A1 | 8/2006 | Miyahara | |
| 2008/0033371 A1 | 2/2008 | Updegraff et al. | |

* cited by examiner

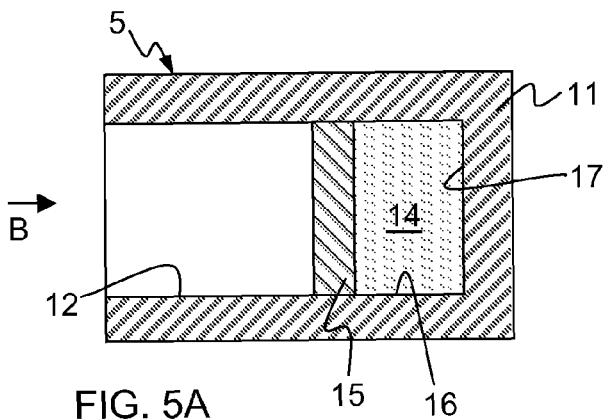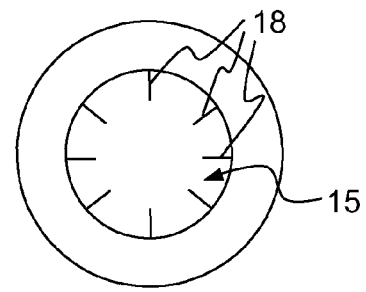
FIG. 5A  FIG. 5B
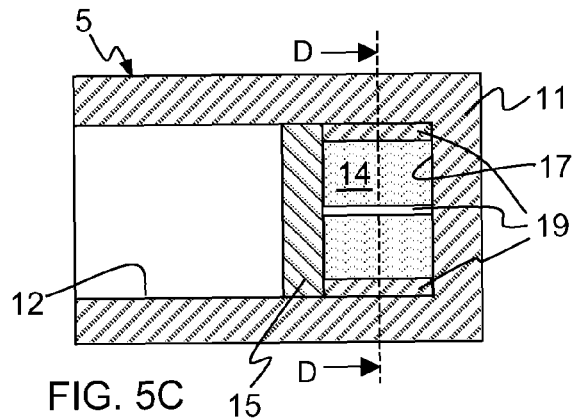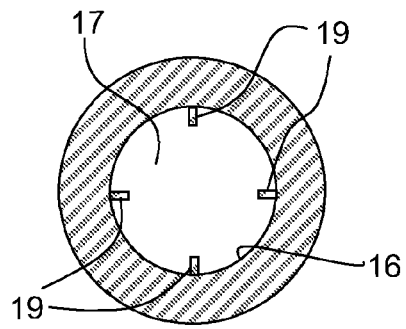
FIG. 5C  FIG. 5D
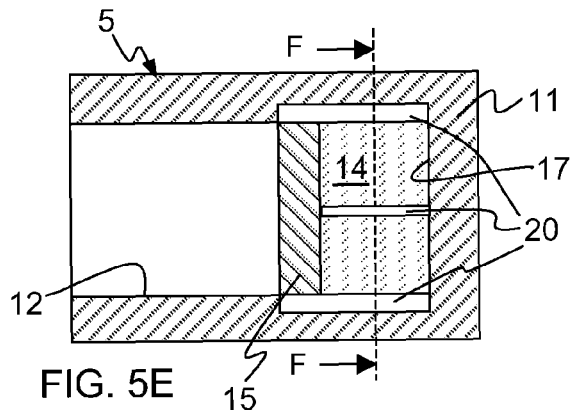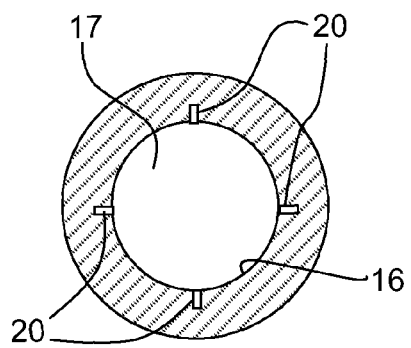
FIG. 5E  FIG. 5F
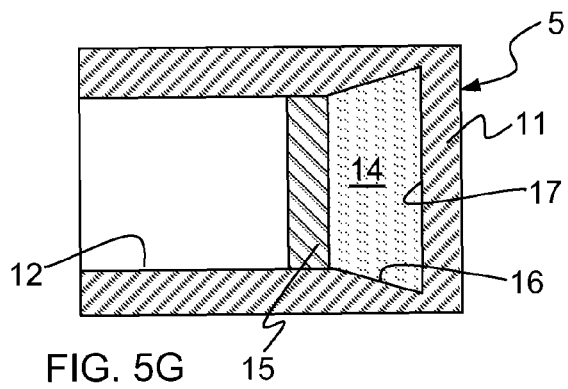
FIG. 5G

MAINTAINING STERILE CONDITIONS IN A FLUID TRANSPORTATION SYSTEM

This application is a national phase application based on PCT/EP2009/057321 filed Jun. 15, 2009, which claims the benefit of Swedish Patent Application No.SE 0801414-4, filed Jun. 17, 2008, and U.S. Provisional Application No. 61/073,051, filed Jun. 17, 2008, the contents of all of which are incorporated herein by reference.

TECHNICAL FIELD

The present invention generally relates to a technique for maintaining sterile conditions in a fluid transportation system. The present invention is, e.g., applicable to medical procedures, including peritoneal dialysis.

BACKGROUND ART

The medical procedure known as peritoneal dialysis has rapidly grown in clinical acceptance as the technique of choice for treating many patients who have lost their kidney function. Typically, the patient is surgically equipped with an implanted catheter ("peritoneal catheter") which communicates between the peritoneal cavity and the exterior. A dialysis solution is passed into the peritoneal cavity through the peritoneal catheter, whereby diffusion takes place between the dialysis solution and the bloodstream across the peritoneal membrane, which is the lining of the peritoneal cavity. The diffusion process removes waste products that are normally excreted through the kidneys, typically solutes such as sodium and chlorine ions and the other materials normally excreted by the body such as urea, creatinine and water. After a certain period of time, the dialysis solution is removed from the peritoneal cavity, carrying with it diffused breakdown products from the bloodstream. Fresh dialysis solution is then passed into the peritoneal cavity through the peritoneal catheter, and this process of filling and emptying is repeated several times.

Thus, peritoneal dialysis typically involves frequent exchange of dialysis solution. This exchange may be performed manually, usually by the patient, or automatically, by an automated dialysis machine.

In the manual technique, known as Continuous Ambulatory Peritoneal Dialysis (CAPD), dialysis solution is constantly present in the patient's abdomen, but is exchanged several times daily. The exchange is performed manually, typically using gravity to move fluid into and out of the peritoneal cavity. In this process, a fluid path is set up between the peritoneal cavity and a container of fresh dialysis solution or a container for receiving spent dialysis solution, by attaching a patient-side connector ("patient connector") to a system-side connector ("system connector") joined with a length of tubing ("line set") that leads to the container(s). Typically, the patient connector is the peritoneal catheter as such or a separate connector in fluid communication with the peritoneal catheter.

In the automatic technique, known as Automated Peritoneal Dialysis (APD), dialysis machines perform the exchanges of dialysis solution. Similarly to CAPD, a fluid path is set up between the patient and the dialysis machine by attaching a patient connector to a system connector joined with a line set of the dialysis machine.

In all techniques of peritoneal dialysis, peritonitis is one of the most significant risks. Peritonitis can result if connections are made between the patient connector and the system connector in a manner which permits even a very small number of micro-organisms to enter the patient connector and to be flushed into the peritoneal cavity.

Accordingly, the frequent connections which must be made and unmade between the patient and system connectors should be performed in a manner which preserves sterile conditions. These connections are typically performed by the patient or by other non-professionals, which increases the risk for incorrect handling and ingress of micro-organisms.

Conventionally, each time the connection is unmade, the connectors are terminated by capping devices. Before attaching the capping devices, a liquid disinfectant is applied manually onto the connectors. This manual sterilization procedure may, even after training of the person handling the connection, involve a significant risk of infection. There is thus a need for a technique that facilitates the handling while decreasing the risk for infections.

U.S. Pat. No. 7,232,419 discloses a system for maintaining sterile connections during dialysis therapy. The system includes a patient connector, a system connector and a so-called cap. The cap is a disposable device which is configured to be arranged intermediate a connected pair of patient and system connectors. Whenever the system connector is separated from the patient connector, the cap remains on the patient connector. A container body, enclosing a fresh sterile cap, is then attached to the disconnected system connector. At this stage, between treatments, the patient is unconnected to the line set and is allowed to move about freely. In order to reconnect to the line set, the patient removes the cap from the patient connector, and removes the container body from the system connector, leaving the sterile cap on the system connector. The exposed patient connector is then attached to the cap on the system connector, thereby causing a port in the system connector to penetrate a septum valve in the cap so as to enable fluid communication through the connectors. During the reconnection procedure, a front end of the patient connector moves or breaks a ring-shaped seal in the cap to release a disinfectant to sterilize the engagement area between the patient connector and the cap.

The procedure of handling both sterile and non-sterile caps, which are being transferred from system connector to patient connector, is complex and far from intuitive. This prior art system may thus be difficult for untrained persons to handle in a correct manner. In fact, the system relies heavily on correct handling, especially when the system connector is to be protected between treatments. If the system connector is handled incorrectly, micro-organisms may enter the system connector before the container body is attached thereto. Since there is no disinfection between treatments, these micro-organisms will prevail and may later enter the fluid path when the port penetrates the septum valve.

SUMMARY OF THE INVENTION

It is an object of the invention to at least partly overcome one or more of the above-identified limitations of the prior art. Specifically, it is an object to provide an improved technique for maintaining sterile conditions in a fluid transportation system. Preferably, the technique should be simple and easy to handle for an untrained user, while providing a low risk for infection.

This and other objects, which will appear from the description below, are at least partly achieved by means of capping devices and methods according to the independent claims, embodiments thereof being defined by the dependent claims.

One inventive concept of the present invention is to provide a capping device configured to be used for terminating a connector when the connector is disengaged from another connector in a fluid transportation system, and at the same time sterilize the terminated connector. Specifically, the capping device is configured to automatically lodge a liquid-containing disinfectant onto relevant portions of the connector, whenever the capping device is engaged with the connector for terminating the same. The liquid-containing disinfectant may, e.g., be a liquid, a liquid dispersion or a gel. Returning to the example of peritoneal dialysis, the capping devices are typically provided as disposable items, allowing the patient to attach one capping device on each of the patient and system connectors, whenever the patient breaks the connection between the connectors. To reconnect, the patient removes the capping devices to expose the sterilized connectors and simply reconnects the connectors. The use of the capping device is intuitive to the user, and therefore provides a low risk of infection.

A first aspect of the invention is a capping device configured to terminate a first connector while disconnected from a second connector in a fluid transportation system, said first connector comprising an exposed surface portion which is enclosed when the first connector is connected to the second connector. The capping device comprises a body defining a chamber with an opening, a liquid-containing disinfectant in the chamber, a sealing element arranged in the opening to form a sealed cavity retaining the disinfectant, and a structure for engaging and guiding the first connector towards the body such that a portion of the first connector displaces the sealing element into the chamber, wherein the sealed cavity is configured such that a displacement of the sealing element into the chamber actively presses the disinfectant out of the sealed cavity, for disinfecting at least part of the exposed surface portion.

In one embodiment, the chamber comprises at least one deformation element arranged to deform the sealing element during at least part of said displacement, so as to define a fluid path for the disinfectant.

In one embodiment, at least one fluid channel is defined in said body for directing the disinfectant onto said surface portion.

In one embodiment, the sealing element comprises a circumferential portion in contact with a cylindrical wall portion of the chamber during said displacement, wherein the disinfectant is pressed to flow past said circumferential portion. The circumferential portion of the sealing element may be resilient, and in one embodiment the circumferential portion is made of resilient material.

In one embodiment, the cylindrical wall portion comprises at least one elongate protrusion for causing a local deformation of the circumferential portion during at least part of said displacement. The at least one protrusion may be elongate and extend in an axial direction of the cylindrical wall portion. Alternatively, the at least one protrusion may be part of a protruding element that extends in a circumferential direction of the cylindrical wall portion while defining at least one gap along its extent.

In one embodiment, the cylindrical wall portion comprises at least one elongate groove, wherein both ends of the groove are uncovered during at least part of said displacement.

In one embodiment, the circumferential portion comprises a cylindrical lip element that abuts on the cylindrical wall portion during said displacement.

In one embodiment, the chamber has an increasing cross-section from said opening in the direction of said displacement, and the sealed cavity is essentially filled with the disinfectant.

In one embodiment, the sealing element comprises an area for engagement with said portion of the first connector, said area being aligned with the geometric centre of the sealing element.

In one embodiment, the chamber is formed as a blind hole in said body, and wherein the sealing element is fitted into the blind hole. The sealing element may be displaceable in the axial direction of the blind hole.

In one embodiment, said portion of the first connector comprises a valve arranged to seal a lumen in the first connector, wherein the sealing element comprises a projection for engaging and opening the valve as the first connector is guided towards the body.

In one embodiment, the disinfectant comprises at least one of: povidone iodine, iodine-containing antimicrobials, and betadine.

In one embodiment, the sealing element comprises at least one rigid protrusion for causing a local deformation of a wall portion of the chamber during at least a part of said displacement, so as to define a fluid path for the disinfectant.

A second aspect of the invention is a capping device configured to terminate a first connector while disconnected from a second connector in a fluid transportation system, said first connector comprising an exposed surface portion which is enclosed when the first connector is connected to the second connector. The capping device comprises: a sealed cavity retaining a liquid-containing disinfectant, and means for causing a portion of the first connector to engage the sealed cavity, so as to actively press the disinfectant out of the sealed cavity, for disinfecting at least part of the exposed surface portion.

A third aspect of the invention is a method for providing a sterile condition of a fluid transportation system. The method comprises: disconnecting a first connector from a second connector in the fluid transportation system; providing at least one capping device according to the first or second aspect; and engaging the first connector and/or the second connector with said at least one capping device.

A fourth aspect of the invention is a method of manufacturing a capping device for terminating a first connector while disconnected from a second connector in a fluid transportation system, said first connector comprising an exposed surface portion which is enclosed when the first connector is connected to the second connector. The method comprises: providing a body that defines a chamber with an opening, said body further comprising a structure for engaging and guiding the first connector towards the body such that a portion of the first connector advances into the chamber; introducing a liquid-containing disinfectant into the chamber through the opening; and arranging a sealing element in the opening to form a sealed cavity retaining the disinfectant, wherein the sealed cavity is configured such that the advancing portion of the first connector displaces the sealing element into the chamber and thereby actively presses the disinfectant out of the sealed cavity, for disinfecting at least part of the exposed surface portion.

Still other objectives, features, aspects and advantages of the present invention will appear from the following detailed description, from the attached claims as well as from the drawings.

BRIEF DESCRIPTION OF THE DRAWINGS

Embodiments of the invention will now be described in more detail with reference to the accompanying schematic drawings.

FIG. 5A is a longitudinal section view of a capping device according to one embodiment, and FIG. 5B is a front view of the capping device as seen in the direction of arrow B in FIG. 5A.

FIG. 5C is a longitudinal section view of a capping device according to another embodiment, and FIG. 5D is a section view taken along line D-D in FIG. 5C.

FIG. 5E is a longitudinal section view of a capping device according to yet another embodiment, and FIG. 5F is a section view taken along line F-F in FIG. 5E.

FIG. 5G is a longitudinal section view of a capping device according to yet another embodiment.

DETAILED DESCRIPTION OF EMBODIMENTS OF THE INVENTION

Figure 1A:
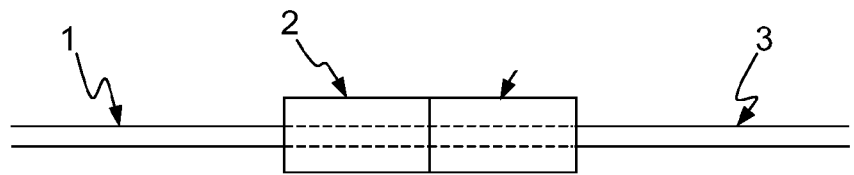
FIGS. 1A-1G are side views that illustrate operational steps during use of an inventive capping device in conjunction with a pair of connectors included in a fluid transportation system.
Figure 1B:
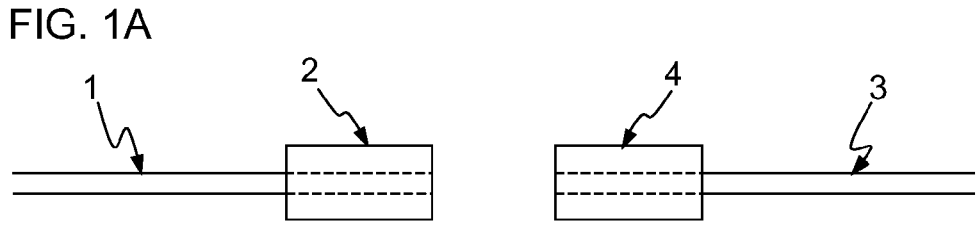
Figure 1C:
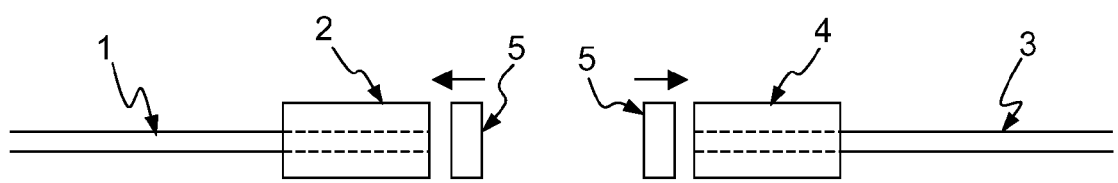

In the following, embodiments of the inventions will be described in the context of peritoneal dialysis. However, the disclosed embodiments as well as the underlying inventive concepts are generally applicable in applications that require sterile conditions, in particular applications that insert a medical fluid into the body of a patient. Examples of other applications where sterile connections are desirably made include the processing of blood and its fractions, the mixing of sterile solutions, connecting catheters with urinary drainage bags, and hemodialysis or blood oxygenation procedures especially with patients who have diminished immunological capability.

The word "sterile" as used herein is intended to include not only its accustomed meaning of a total absence of living micro-organisms, but also is intended to include the concept of substantial sterility, in which the number of micro-organisms is reduced to such a low population that the likelihood of infection or contamination, e.g., peritonitis in the case of peritoneal dialysis, is substantially reduced or eliminated.

Throughout the following description, like elements are indicated by the same reference numerals.

FIG. 1 illustrates steps of a method for maintaining sterile conditions in a fluid transportation system. The fluid transportation system includes a first tubing portion 1 joined to a first connector 2, and a second tubing portion 3 joined to a second connector 4. In an initial state, shown in FIG. 1A, the first and second connectors 2, 4 are connected to form a fluid path (indicated by dotted lines) between the first tubing portion 1 and the second tubing portion 3. In FIG. 1B, the first and second connectors 2, 4 are disengaged, thereby exposing surface portions of the first and second connectors 2, 4. In order to preserve sterile conditions in the fluid transportation system, a respective capping device 5 is attached (FIG. 1C) to each of the connectors 2, 4 so as terminate the same and to cover the exposed surface portions (FIG. 1D). As will be explained in the following, the capping device 5 is configured to automatically lodge an amount of liquid-containing disinfectant onto the exposed surface portions when the capping device 5 is mounted on the connector 2, 4.

Figure 1D:
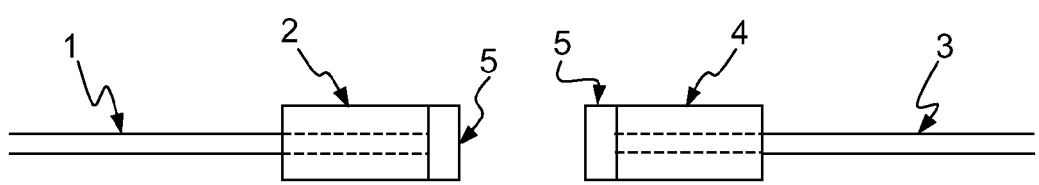

Typically, the first connector 2 is in fluid communication with a patient. In the example of peritoneal dialysis, the first connector 2 may be a patient catheter or any other type of connector in fluid communication with the patient catheter. The second connector 4 may be a distal end of a line set in fluid communication with a source of dialysis solution. Thus, the first connector 2 may be a patient connector and the second connector 4 may be a system connector. By terminating the patient connector 2 with the capping device 5, as shown in FIG. 1D, the patient is allowed to move around freely, while minimizing the risk for infections.

Figure 1E:
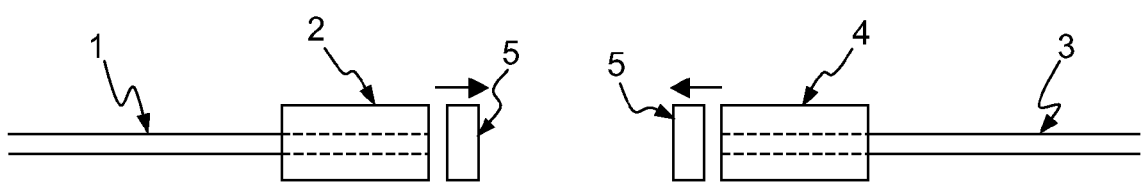
Figure 1F:
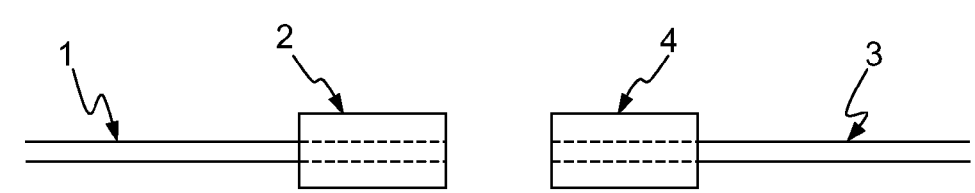
Figure 1G:
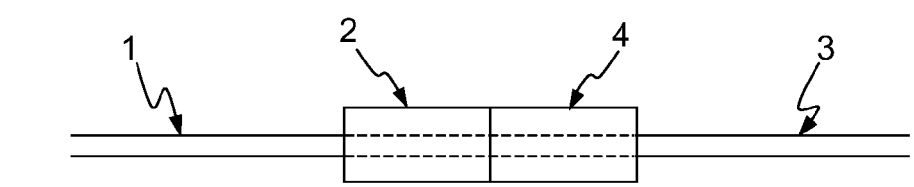

FIGS. 1E-1G illustrate subsequent steps for re-engaging the first and second connectors 2, 4, in which the capping devices 5 are removed from the first and second connectors 2, 4 (FIG. 1E). The thus-exposed surface portions are now sterile by the action of the disinfectant. The connectors 2, 4 are then brought into engagement (FIG. 1F) to establish a fluid path through the first and second connectors 2, 4 (FIG. 1G).

In certain applications, the system connector 4 need not be terminated by a capping device, e.g. if the system connector is replaced by a new (suitably sterile) system connector in the procedure of disengaging and re-engaging the connectors. Alternatively, other known techniques could be used to sterilize the system connector before reconnecting it to the patient connector.

Figure 2:
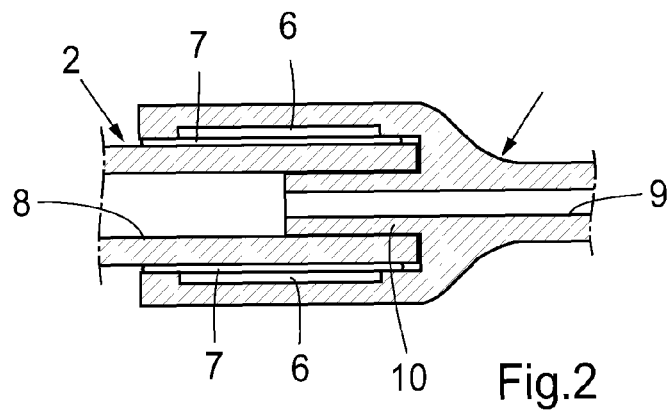
FIG. 2 is a section view of an exemplifying pair of connectors which are connected to establish an internal fluid path.

FIG. 2 is a cross-section of an exemplifying pair of first and second connectors 2, 4, which are connected to set up an internal fluid path. In this example, the first connector 2 is a male-type connector with external engagement means 7, and the second connector is a female-type connector with internal engagement means 6. The engagement means 6, 7 could be any of a variety of mutually engaging constructions such as, for example, threaded fitments, luer connections, friction fits, and snap fittings. The first and second connectors 2, 4 define a respective lumen 8, 9. When the first connector 2 is brought into engagement with the second connector 4, an internal projection 10 of the second connector 4 enters the lumen 8 of the first connector 2 to establish a fluid path through the connectors. The external surface of the projection 10 may or may not form a luer fitting with the distal end of lumen 8.

Figure 3A:
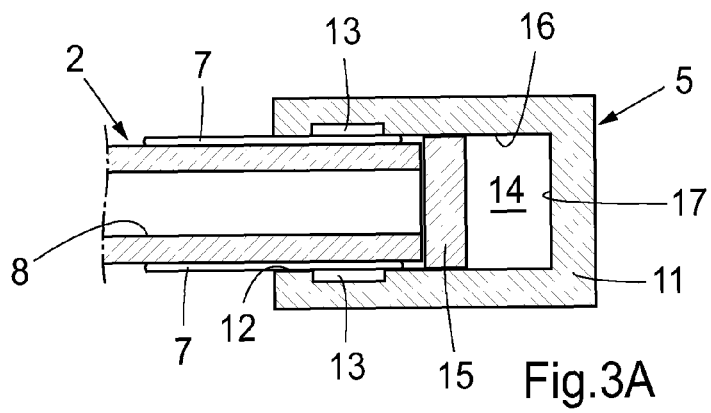
FIGS. 3A-3C are section views of a capping device in three different stages of mounting on one of the connectors in FIG. 2.
Figure 3B:
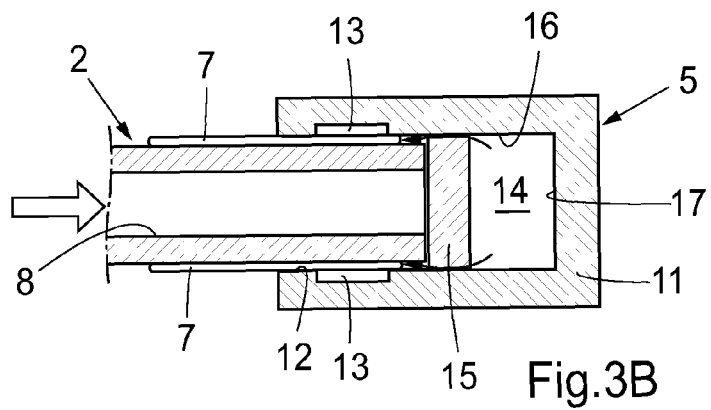
Figure 3C:
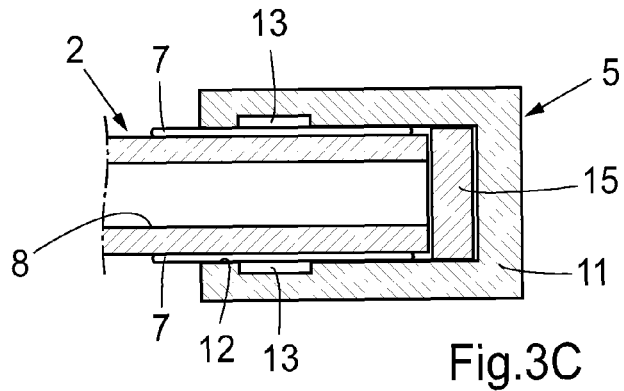

FIGS. 3A-3C illustrate the procedure of mounting a capping device 5 onto the exposed end of the first connector 2 in FIG. 2. In the example of FIG. 3A, the capping device 5 comprises a body 11 that defines an elongate bore 12 with a bottom, i.e. a blind-hole. The bore 12 is adapted to receive the exposed front end of first connector 2, with engagement means 13 being provided inside the bore 12 and adapted to engage with the external engagement means 7 of the first connector 2. The bore 12 has an essentially uniform cross-section in its axial direction. A sealed cavity 14 is formed at the inner end portion of the bore, by a seal or sealing element 15 being fitted into the bore 12. The cavity 14 is thus defined by the seal 15, a cylindrical wall portion 16 and a bottom end surface 17. The cavity 14 is wholly or partly filled with a liquid-containing disinfectant.

As indicated by the block arrow in FIG. 3B, the capping device 5 is advanced onto the first connector, or vice versa. In this process, the front end of the first connector 2 engages and displaces the seal 15 towards the end surface 17. Thereby, the pressure inside the cavity 14 increases, and eventually the disinfectant is actively pressed out of the cavity 14 and caused to flow past the interface between the seal 15 and the cylindrical wall portion 16 onto the engagement means 7 (as indicated by arrows in FIG. 3B). When the capping device 5 is fully mounted on the first connector 2, as shown in FIG. 3C, a substantial portion of the disinfectant has been ejected onto the engagement means 7. Thus, by mounting the capping device 5, the end portion of the first connector 2 is both terminated and disinfected.

In this, as well as in other embodiments, it may be advantageous to arrange the seal with respect to the connector such that the displacement force is applied in, or at least symmetrically to, the geometric centre of the seal. This may reduce the risk for jamming of the seal.

Figure 4:
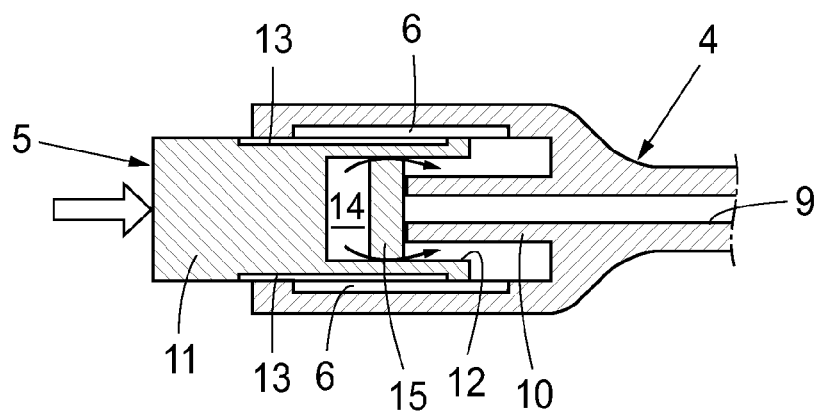
FIG. 4 is a section view of a capping device during mounting on the other connector in FIG. 2.

FIG. 4 illustrates a capping device 5 which is mounted onto the exposed end of the second connector 4 in FIG. 2. The capping device has the same construction as the capping device in FIG. 3, except that the engagement means 13 are provided on the outer periphery of the body 11 instead of inside the bore 12. As the capping device 5 is advanced onto the second connector 4, the front end of the projection 10 engages the seal 15 and actively presses disinfectant out of the sealed cavity 14 and onto the external surface of the projection 10 (as indicated by arrows in FIG. 4). As the capping device 5 is advanced further, the disinfectant is directed onto the engagement means 6 as well.

It should be realized that the capping device 5 might be designed for use with existing types of connectors. Thus, the inventive capping device makes it possible to obtain sterile conditions in existing fluid transportation systems, without requiring any modifications of these systems. However, in alternative embodiments, one or more of the connectors 2, 4 may be tailored to match a specific type of capping device 5.

It should also be understood that, in all embodiments disclosed herein, either one of the connectors 2, 4 could be used as patient connector.

FIGS. 5A-5G illustrate different configurations of the sealed cavity 14 inside the capping device 5, with the engagement means 13 being omitted for ease of illustration.

In FIG. 5A, like in FIG. 3, the cavity 14 is cylindrical and formed between a disk-shaped seal 15 and the bottom end surface 17. The cavity 14 has an essentially invariant cross-section along the bore 12, so that a circumferential portion of the seal 15 abuts the cylindrical wall portion 16 of the bore 12 while the seal 15 is displaced into the cavity 14. The seal 15, or at least its circumferential portion, may be resilient, so as to facilitate the outflow of disinfectant from the cavity 14 and/or to prevent jamming, as the seal is pressed towards the end surface 17. Alternatively or additionally, as shown in the front view of FIG. 5B, the seal 15 may include one or more perforations or notches 18 that allow disinfectant to escape the cavity 14 as the pressure therein increases. This may provide for a well-defined fluid path for the disinfectant. The perforations/notches 18 may be located to direct the outflowing disinfectant onto a specific portion of the connector. In the illustrated example, the perforations/notches 18 are located in the circumferential portion of the seal 15.

FIGS. 5C-5D illustrate an alternative embodiment, in which the cylindrical wall portion 16 that defines the cavity includes a fixed deformation means 19 which is arranged to locally deform the seal 15 while it is displaced into the cavity 14. In the illustrated example, the deformation means 19 is implemented by four longitudinally extending ribs that are distributed circumferentially on the cylindrical wall portion 16. The local deformation of the seal 15 creates a well-defined fluid path for the disinfectant, which is allowed to escape the cavity through one or more channels formed in the seal 15 by the deformation means 19. It has also been found that the force required to displace the seal 15 into the cavity 14 may be reduced by the provision of deformation means 19. The reduced force may facilitate mounting of the capping device 5. Furthermore, the deformation means 19 may act as a stop or shoulder that defines the initial position of the seal 15. Such a stop/shoulder may facilitate the manufacture of the capping device, as will be further described below. Generally, the deformation means 19 may be in the form of one or more protrusions on the cylindrical wall portion 16, with the protrusion(s) being arranged to cause a local deformation of the circumferential portion of the seal 15 during at least part of its displacement into the cavity 14.

FIGS. 5E-5F illustrate yet another alternative embodiment, in which one or more grooves 20 (four shown) are defined in the cylindrical wall portion 16 so as to form fluid channels that lead the disinfectant onto the connector when the seal 15 is urged towards the cavity 14. In the initial position, shown in FIG. 5E, the channels are closed off by the seal 15. As the seal 15 is displaced towards the end surface 17 and/or as the increasing liquid pressure displaces the periphery of the seal radially away from the grooves 20, the channels are uncovered and the disinfectant will be actively pressed out of the cavity 14 via the channels. Instead of grooves 20 opening into the cylindrical wall portion 16 along their entire length, the channels may be wholly or partly confined inside the wall material. However, it is currently believed that it may be simpler to incorporate grooves than confined channels in the capping device.

FIG. 5G illustrates yet another embodiment, in which the cavity 14 has an expanding cross-section along the bore 12 in a direction away from the seal 15. The cavity 14 is essentially filled with disinfectant. Thus, as the seal 15 is urged towards the cavity 14, the disinfectant will be actively pressed out of the cavity 14 along the periphery of the seal 15.

It is to be understood that different features discussed above in relation to FIGS. 5A-5G could be combined in one and the same embodiment. For example, a deformation means 19 could be combined with perforations/notches 18 in the seal 15 and/or with grooves 20 in the cylindrical wall portion 16.

It is also to be realized that except for the configuration of FIG. 5G, the disinfectant need not fill the entire cavity 14. In fact, the cavity 14 can have any degree of filling, as long as a sufficient amount of disinfectant is released to adequately disinfect the relevant parts of the connector.

Figure 6A:
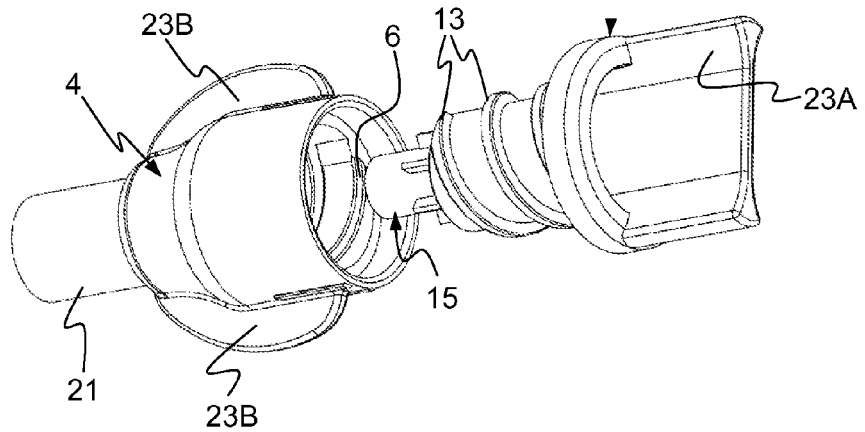
FIG. 6A is a perspective view of a female-type connector and a corresponding capping device in an initial stage of mounting.
Figure 6B:
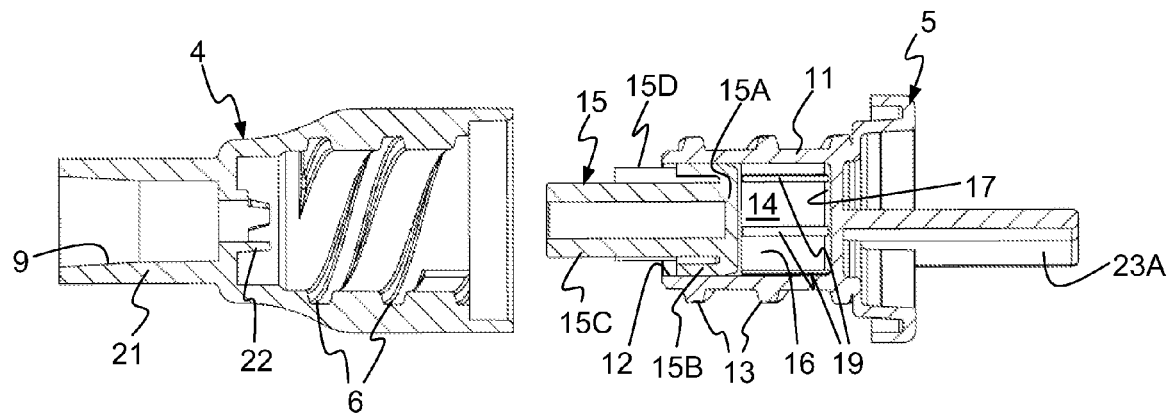
FIGS. 6B-6C are longitudinal section views of the connector and the capping device in the initial stage and in a final stage, respectively, of mounting.
Figure 6C:
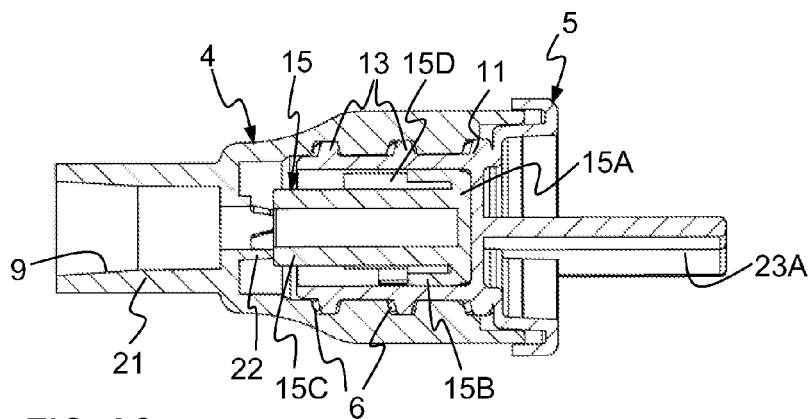

FIGS. 6A-6C illustrate yet another example of a capping device 5 configured to cooperate with a female-type connector 4 having a connection portion with internal threads 6. The connector 4 also has a rear sleeve 21 for attachment of tubing.

The sleeve 21 defines an internal lumen 9 that opens into the connection portion via a protrusion 22.

FIGS. 6A and 6B show the capping device 5 before it is engaged with the connector 4.

The capping device 5 comprises a cylindrical body portion with external threads 13 adapted to engage with the internal threads 6 of the connector 4. An elongate bore 12 of uniform cross-section is defined in the cylindrical body portion. The sealed cavity 14, which holds a liquid-containing disinfectant, is defined by a seal 15 which is composed of a disk 15A with a cylindrical lip or flange 15B for abutment on the cylindrical wall portion 16. The lip 15B may be pre-formed into the cylindrical shape shown in FIGS. 6B-6C. Alternatively, the lip 15B may be folded into the illustrated shape by its engagement with the cylindrical wall portion 16 when the seal is inserted into the bore 12. The combination of disk 15A and lip 15B provides a low-weight seal that has a large sealing area at the interface between the seal 15 and the cylindrical wall portion 16. This has been found to reduce the risk of jamming and minimize any uncontrolled outflow of disinfectant both before and during the displacement. Like in FIGS. 5C-5D, the outflow of disinfectant is controlled by elongate deformation ribs 19 projecting from the cylindrical wall portion 16.

The seal 15 further comprises a rod or piston 15C which is connected to the disk 15A in alignment with its geometric centre and which is brought into engagement with the protrusion 22. As shown, the rod 15C may be hollow to reduce the weight of the seal and/or to save costs by reducing the amount material needed to produce the seal. The rod 15C is provided to adapt the capping device 5 to the connector 4, specifically to coordinate the engagement between the threads 6, 13 with the engagement between the seal 15 and the connector 4.

Figure 11A:
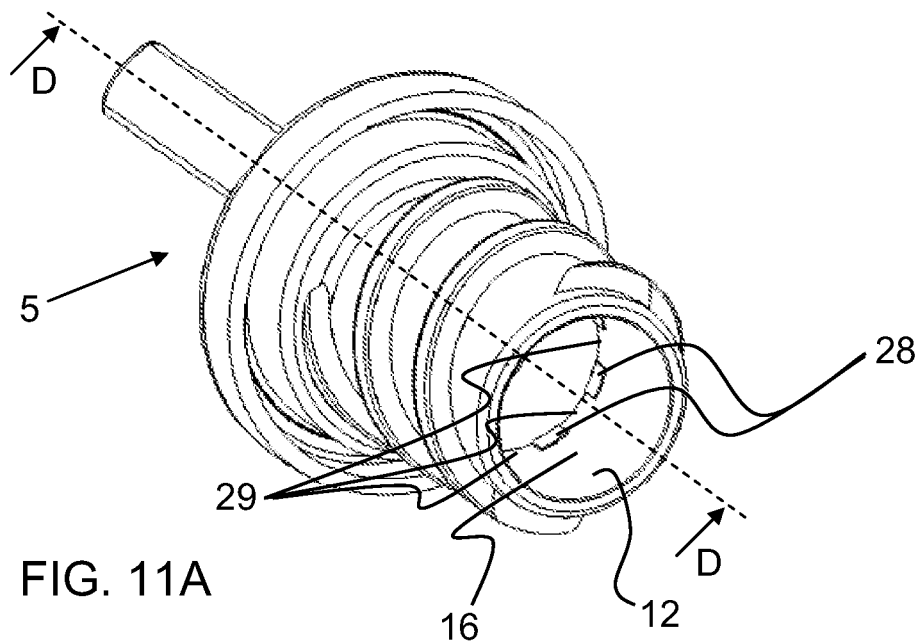
FIG. 11A is a perspective view and FIG. 11B is a longitudinal section view taken along line D-D in FIG. 11A of a capping device according to another embodiment.
Figure 11B:
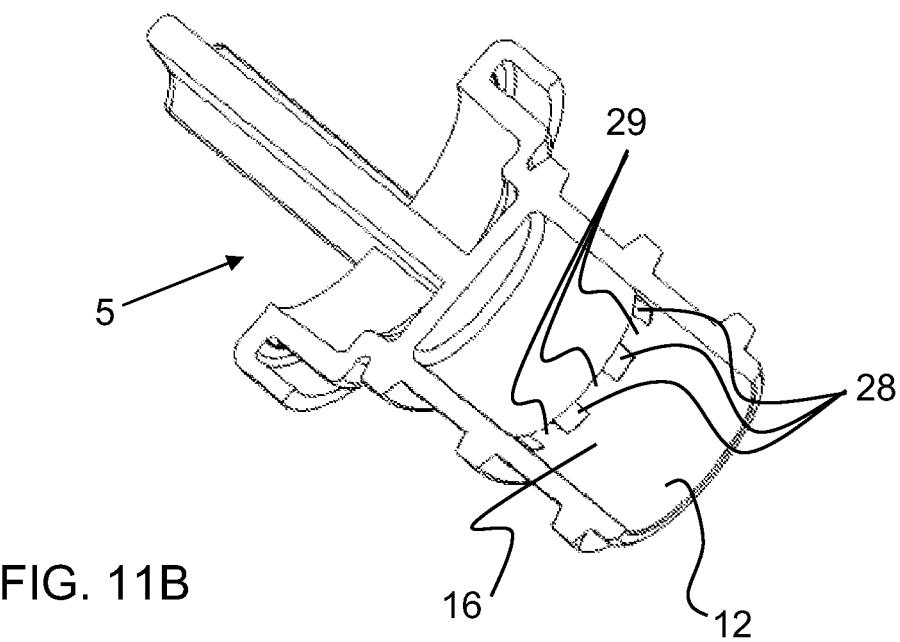

A variant of the capping device 5 is shown in FIGS. 11A-11B. In this variant, the capping device 5 comprises a deformation element which protrudes from wall portion 16 along part of its circumference. In the illustrated embodiment, the deformation element defines a plurality of protrusions or teeth 28 which are spaced by openings or gaps 29, i.e. portions with less or no protrusion from the wall portion 16. In an alternative embodiment (not shown), the deformation element is configured as a broken annulus, i.e. a single protrusion with a single opening. Similarly to the deformation ribs 19 of the embodiments shown in FIG. 5C and FIGS. 6A-6C, the deformation element 28 locally deforms the seal 15 while it is displaced into the capping device 5 so as to create one or more fluid paths for the disinfectant through the opening(s) 29 in the deformation element.

Figures 7A, 7B:
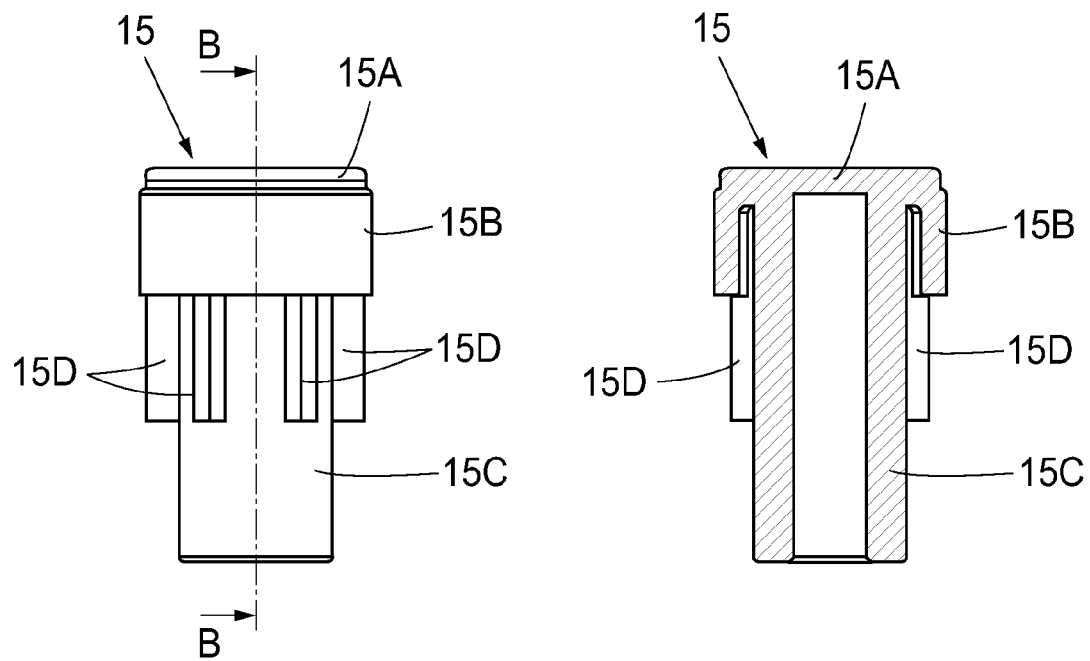
FIG. 7A is an elevated side view of a seal.
FIG. 7B is a section view taken along line B-B in FIG. 7A.

One embodiment of the seal 15 is shown in further detail in FIGS. 7A-7B. The illustrated seal 15 comprises the above-mentioned combination of a disk 15A, a lip 15B and a hollow rod 15C. The seal 15 is also provided with means for preventing misalignment of the seal during its displacement into the sealed cavity 14, e.g. to reduce the risk of jamming. These means are provided in the form of longitudinal guiding ribs 15D on the outer periphery of the rod 15C. The ribs 15D have a radial extension (height) that provides a small spacing to the cylindrical wall portion 16 (see FIG. 6C). If the seal 15 tends to tilt during its displacement, the ribs 15D engage the wall portion 16 to thereby prevent further tilting. Suitably, at least three ribs 15D are evenly distributed across the circumference of the rod 15C, with each rib 15D having a limited thickness (i.e. extent in the circumferential direction of the rod 15C). The limited rib thickness provides for a low frictional resistance during the displacement, since only a limited surface area may engage the wall portion 16 even if the seal 15 is tilted. The frictional resistance is further reduced by spacing the ribs 15D from the wall portion 16.

Figure 10A:
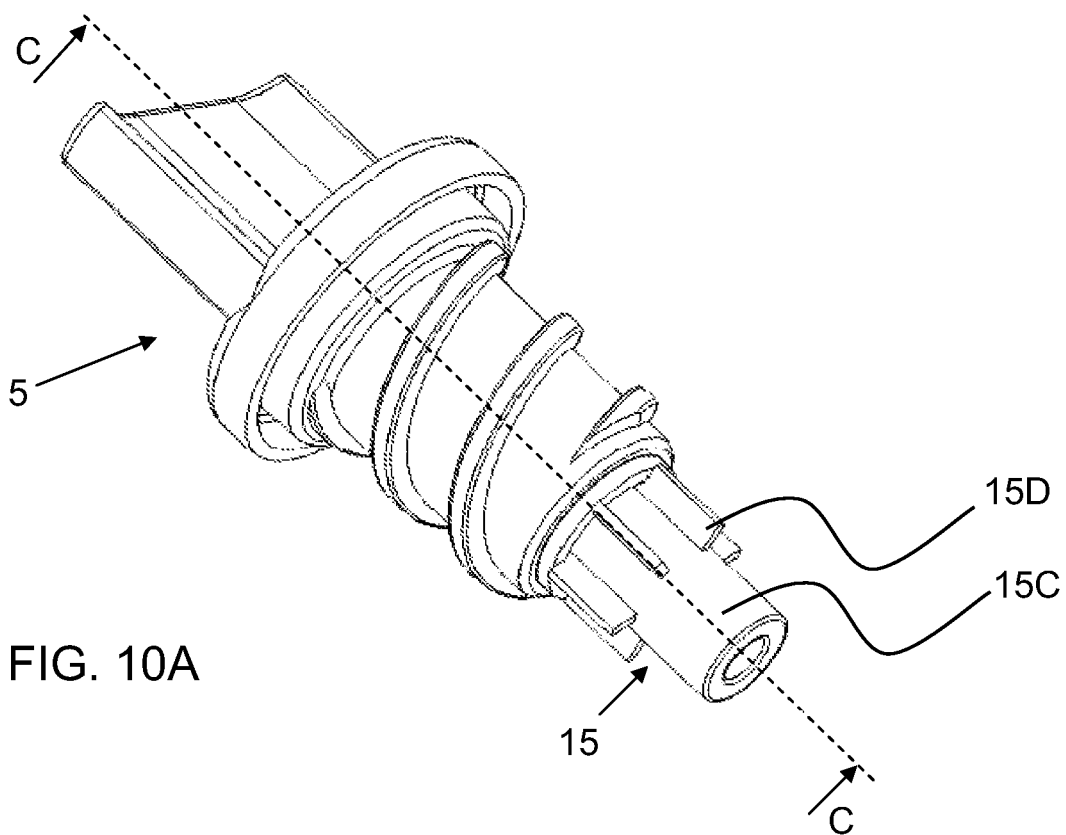
FIG. 10A is a perspective view and FIG. 10B is a longitudinal section view taken along line C-C in FIG. 10A of a capping device according to one embodiment.
Figure 10B:
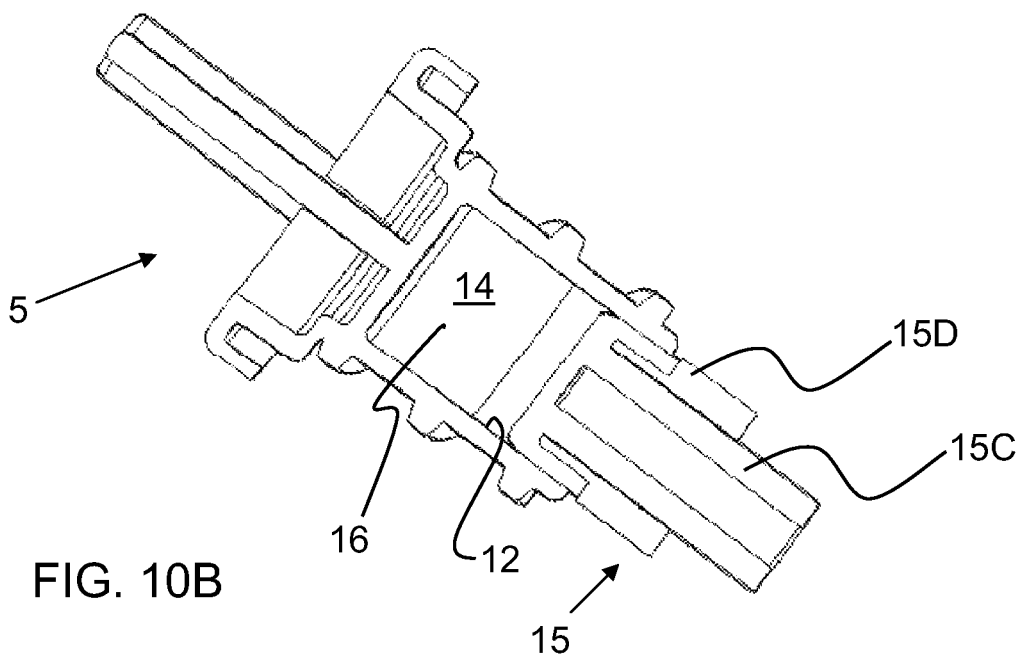

Another embodiment of the seal 15 is shown in further detail in FIGS. 10A-10B. The means for preventing misalignment of the seal during its displacement into the sealed cavity 14 are also configured to act as deforming elements. These means are also provided in the form of longitudinal ribs 15D on the outer periphery of the rod 15C. In this embodiment, the rod 15C and the ribs 15D are made of a rigid or incompressible material, such as metal or a suitable plastic material. The ribs 15D have such a radial extension or height that they extend slightly beyond the cylindrical wall portion 16, when the seal 15 is mounted in the bore 12. When the seal 15 is displaced in the bore 12, the ribs 15D deform the wall portion 16 to create a fluid path for the disinfectant in the cavity 14. Hence, the ribs 15D constitute deformation elements at a back end of the seal 15. The radial extension of the ribs 15D may be 0.03-0.10 mm, preferably 0.04-0.06 mm, beyond the cylindrical wall portion 16 of the bore 12 to provide sufficient deformation or widening of the wall portion 16, while also providing sufficient friction to allow displacement and prevent springing back. In this embodiment, it is thus the cylindrical wall portion 16 of the bore 12 that provides the flexibility necessary to allow for disinfectant to be pressed to flow past the circumferential portion of the seal 15. The wall portion 16 may be provided as a flexible lining inside the bore 12. Alternatively, the bore-defining portion of the capping body may be made of a sufficient flexible material.

Figure 12:
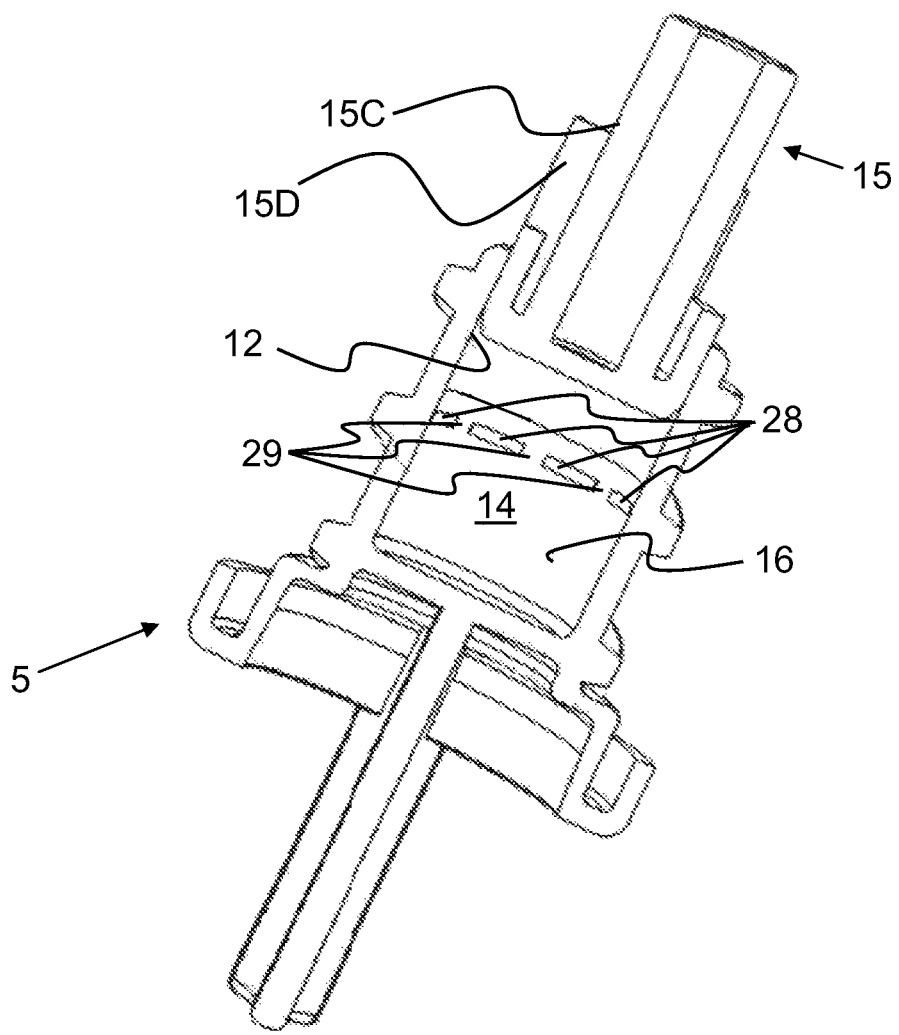
FIG. 12 is a longitudinal section view of a capping device according to a combination of the embodiments in FIGS. 10A-10B and FIGS. 11A-11B.

A combination of the embodiments of FIGS. 10A-10B and 11A-11B is shown in FIG. 12. In the illustrated embodiment, the ribs 15D of the seal 15 and the ribs 28 on the cylindrical wall portion 16 acts as deformation elements that co-operate to ensure deformation of the wall portion 16 so that one or more fluid paths is created when the seal 15 is displaced into the bore 12. In fact, the ribs 28 in the bore 12 and ribs 15D on the seal 15 are arranged to conjointly deform the seal 15 and to cause a local deformation of the cylindrical wall portion 16 of the bore 12 during at least a part of the displacement, so as to define a fluid path for the disinfectant.

Returning to FIG. 6, the capping device 5 further comprises a grip portion 23A in the form of a flange that can be gripped by a user in order to screw the capping device 5 in and out of the connector 4. Similarly, the connector 4 comprises a grip portion 23B formed by a pair of opposite wings that can be gripped by the user.

The capping device 5 is mounted on the connector by inserting the threaded body portion into the connection portion. By turning the capping device 5 in relation to the connector 4, the threads 6, 13 engage and advance the capping device 5 towards the connector 4. In this process the seal 15 is displaced axially in the bore, causing the disinfectant to be pressed out of the cavity 14 via channels that are formed in the lip 15B by the ribs 19. FIG. 6C shows the capping device 5 when fully inserted into the connector 4. In the illustrated final position, all disinfectant has been pressed out of the cavity 14 to disinfect the connection portion.

Figure 8A:
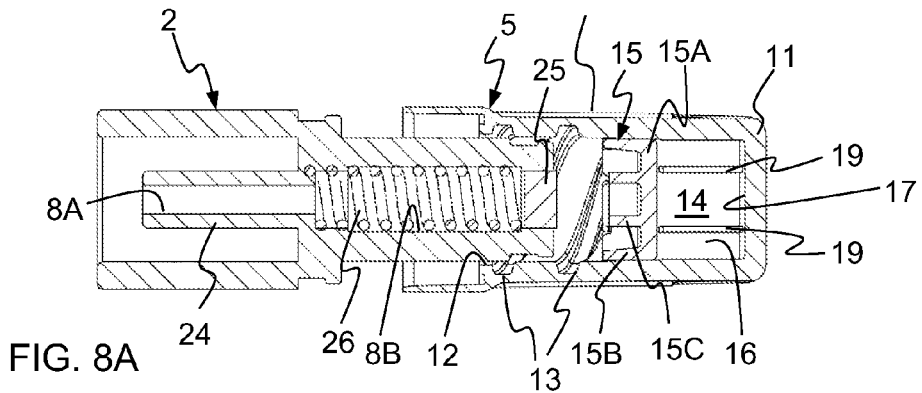
FIGS. 8A-8B are longitudinal section views of a male-type connector and a corresponding capping device in an initial stage and a final stage, respectively, of mounting.
Figure 8B:
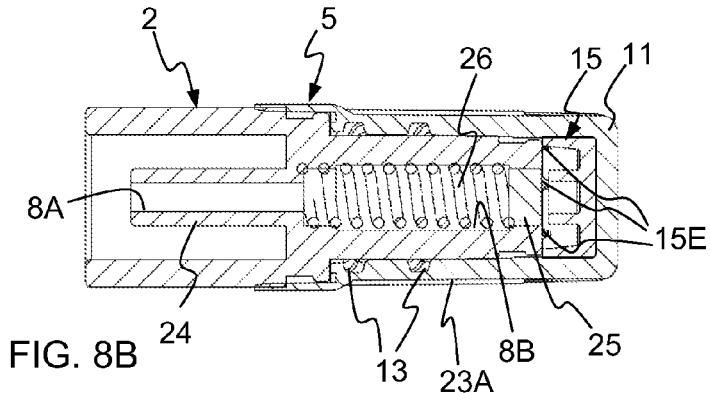
Figures 8C, 8D:
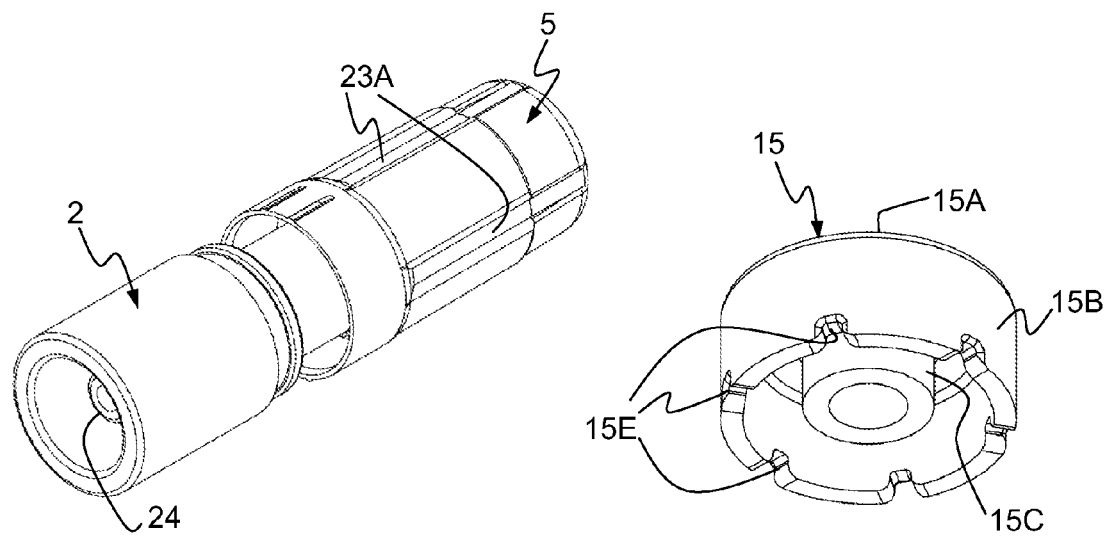
FIG. 8C is a perspective view corresponding to FIG. 8A.
FIG. 8D is a perspective view of a seal arranged in the capping device of FIGS. 8A-8B.

FIGS. 8A-8C illustrate yet another example of a capping device 5 configured to cooperate with a male-type connector 2 having a connection portion with external threads (not shown). The connector has a rear sleeve 24 for attachment of tubing, e.g., in communication with a patient catheter. The sleeve 24 defines a first lumen portion 8A that opens into a second lumen portion 8B inside the connection portion. A valve 25 is arranged in the front end of the connector 2 to close the lumen portion 8B. This valve 25 is opened when the connector 2 is fitted onto a corresponding female connector, by an element of the female connector (cf. projection 22 in FIG. 6) pushing the valve 25 into the lumen portion 8B against the action of a spring 26 mounted inside the lumen portion 8B.

The capping device 5 includes a body 11 that defines a longitudinal bore. Similarly to the other embodiments disclosed herein, a seal 15 is arranged in the bore to define a sealed cavity 14. The proximate end of the bore is provided with internal threads 13 for engagement with the threads on the connector 2. The design of the cavity 14, as well as the use and operation of the capping device 5, have already been discussed above in relation to FIG. 6 and will therefore not be repeated. FIG. 8A shows the capping device 5 before it is engaged with the connector 2, and FIG. 8B shows the capping device 5 when fully inserted into the connector 2. FIG. 8C is a perspective view of the capping device 5 during mounting. The outer periphery of the capping device 5 is provided with a grip portion 23A containing longitudinal grooves to increase the friction between the capping device 5 and a user's hand when the capping device 5 is to be screwed onto the connector 2.

As indicated in FIGS. 8A-8B, and shown more clearly in the perspective view in FIG. 8D, the seal 15 is provided with a number of recesses 15E in the peripheral end of the lip 15B. As the front end of the connector 2 engages the peripheral end of the lip 15B, so as to urge the seal 15 towards the cavity 14, the recesses 15E define openings that allow the ejected disinfectant to also reach and disinfect the front end of the connector 2.

Figure 9A:
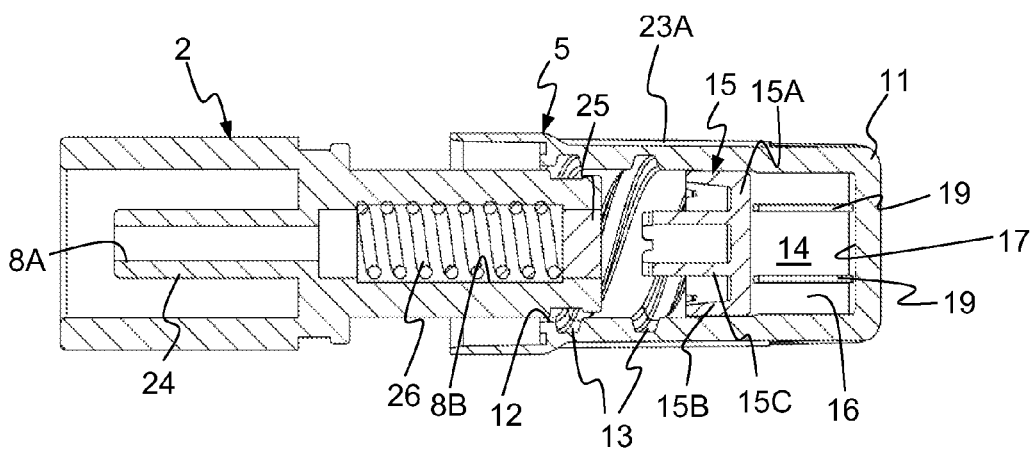
FIGS. 9A-9B illustrate the mounting of an alternative capping device on the male-type connector of FIGS. 8A-8B.
Figure 9B:
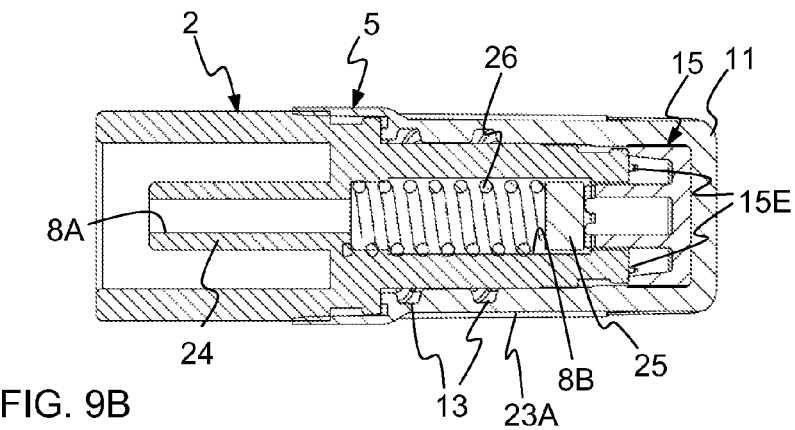

FIGS. 9A-9B show a variant of the embodiment in FIGS. 8A-8C, in which the rod 15C of the seal 15 is extended such that the valve 25 is opened as the connection portion is advanced into the bore, as shown in FIG. 9B. By such a design, the valve 25 and the front part of the lumen portion 8B may also be subjected to the ejected disinfectant, by the disinfectant flowing through the recesses 15E in the seal 15 onto the front end of the connector 2.

Common to all embodiments and exemplary configurations disclosed in the foregoing is that the disinfectant is actively pressed out of the sealed cavity to disinfect at least part of an exposed surface portion of the first/second connector. The exposed surface portion is a portion of the first/second connector that is exposed upon disconnection from the second/first connector and that is enclosed by reconnection to the second/first connector. The exposed surface portion may include the engagement means for interconnecting the first and second connectors. Preferably, but not necessarily, the sealed cavity is configured such that the disinfectant is ejected onto the exposed surface portion.

All embodiments may further include a feedback means (not shown), which is adapted to give an audible, tactile or visual indication when the capping device is properly mounted on the connector. Such a feedback means for audible and/or tactile feedback may be configured as cooperating teeth and protrusions, groves and projections, snap-fits, etc, between the capping device 5 and the connector 2, 4.

Generally, the body 11 of the capping device 5 is made of one or more plastic materials such as polyethylene, polypropylene, nylon, polystyrene, polyester, PVC, a blend of various plastics or any other plastic or synthetic material that is capable of being washed and sterilized. In a variation, all or part of the body is constructed from metal, e.g. a non-corrosive metal such as stainless steel or aluminium. The seal 15 is generally made from compressible materials such as compressible polymer, such as silicone, neoprene, vinyl, viton, Buna-N, butyl, EPDM, latex or the like, or a polymer with an added softening agent. The disinfectant may be of any suitable type and amount that can sterilize plastic, rubber, metal or other like materials. The disinfectant contains a liquid, which implies that the disinfectant may be a pure liquid, a liquid dispersion, a gel, etc. The disinfectant may e.g. contain or be composed of at least one of povidone iodine, iodine-containing antimicrobials, and betadine. In other examples, the disinfectant may contain or be composed of at least one of an alcohol, an aldehyde, paracetic acid, performic acid, polyaminopropyl biguanide, iodophor, quaternary ammonium compounds, phenolics, chlorhexidine, hexachlorophene, chlorine dioxide, a chlorine based solution, and a sodium hypochlorite solution such as Amuchina. In the exemplifying embodiments shown in FIGS. 6-9, an amount of about 0.3-0.6 ml povidone iodine is contained in the sealed cavity.

In all embodiments, the bore and the sealed cavity can have any type of cross-section, e.g. circular, elliptical, polygonal, etc.

The components of the capping device may be constructed into desired shapes via any known method for producing plastic or rubber pieces, such as molding (e.g. injection molding, transfer molding, compression molding), machining, cutting, stamping, etc. The body of the capping device may be formed as a unitary piece, or it may be composed of separate pieces that are assembled by using coupling elements, adhesive, ultrasonic welding, etc. Similarly, the seal may be either formed as a unitary piece or an assembly of separate pieces.

When the body and the seal have been formed, and possibly sterilized, the capping device can be produced by simply introducing the disinfectant into the bore, and then pushing the seal into its proper position inside the bore to form the sealed cavity. The proper position may be defined by the aforesaid deformation means, which may act as a shoulder or stop that defines the position of the seal. The resulting capping device may then again be sterilized, before being encased in a sterile pack or wrapping for distribution.

The inventive concept has mainly been described above with reference to a few embodiments. However, as is readily appreciated by a person skilled in the art, other embodiments than the ones disclosed above are equally possible within the scope and spirit of the invention, which is defined and limited only by the appended patent claims.

The invention claimed is:

1. A capping device configured to terminate a first connector while disconnected from a second connector a fluid transportation system, said first connector comprising an exposed surface portion, said exposed surface portion being enclosed when the first connector is connected to the second connector, said capping device comprising:
   a body defining a chamber with having an opening;
   a liquid-containing disinfectant in the chamber;
   a sealing element arranged in the opening to form a sealed cavity retaining the disinfectant; and
   a structure configured to engage and guide the first connector towards the body such that a portion of the first connector displaces the sealing element into the chamber,
   wherein
      a circumferential portion of the sealing element is in continuous contact with a cylindrical wall portion of the chamber during a displacement of the sealing element into the chamber, and
      the sealed cavity is configured such that the displacement of the sealing element into the chamber causes a pressure inside the sealed cavity to increase, thereby actively pressing the disinfectant out of the sealed cavity and on to at least part of the exposed surface portion.

2. The capping device of claim 1, wherein the chamber comprises at least one deformation element arranged to deform the sealing element during at least part of said displacement, so as to define a fluid path for the disinfectant.

3. The capping device of claim 1, wherein at least One fluid channel is defined in said body, said at least one fluid channel being configured to direct the disinfectant onto said exposed surface portion.

4. The capping device of claim 1, wherein the sealing element comprises a circumferential portion in contact with a cylindrical wall portion of the chamber during said displacement, wherein the disinfectant is pressed to flow past said circumferential portion.

5. The capping device of claim 4, wherein at least the circumferential portion of the sealing element is resilient.

6. The capping device of claim 5, wherein the circumferential portion is made of resilient material.

7. The capping device of claim 4, wherein the cylindrical wall portion comprises at least one protrusion configured to cause a local deformation of the circumferential portion during at least part of said displacement.

8. The capping device of claim 7, wherein said at least one protrusion is elongate and extends in an axial direction of the cylindrical wall portion.

9. The capping device of claim 7, wherein said at least one protrusion is part of a protruding element that extends in a circumferential direction of the cylindrical wall portion while defining at least one gap along the extent of the cylindrical wall portion.

10. The capping device of claim 4, wherein the cylindrical wall portion comprises at least one elongate groove having first and second ends, wherein both of said first and second ends of the groove are uncovered during at least part of said displacement.

11. The capping device of claim 4, wherein the circumferential portion comprises a cylindrical lip element that abuts on the cylindrical wall portion during said displacement.

12. The capping device of claim 1, wherein the chamber has an increasing cross-section from said opening in the direction of said displacement, and wherein the sealed cavity is essentially filled with the disinfectant.

13. The capping device of claim 1, wherein the sealing element comprises an area configured to engage said portion of the first connector, said area being aligned with a geometric centre of the sealing element.

14. The capping device of claim 1, wherein the chamber is formed as a blind hole in said body, and wherein the sealing element is fitted into the blind hole.

15. The capping device of claim 14, wherein the sealing element is displaceable in the axial direction of the blind hole.

16. The capping device of claim 1, wherein said portion of the first connector comprises a valve arranged to seal a lumen in the first connector, wherein the sealing element comprises a projection configured to engage and open the valve as the first connector is guided towards the body.

17. The capping device of claim 1, wherein The disinfectant comprises at least one of: povidone iodine, iodine-containing antimicrobials, and betadine.

18. The capping device of claim 1, wherein the sealing element comprises at least one rigid protrusion configured to cause a local deformation of a wall portion of the chamber during at least a part of said displacement, so as to define a fluid path for the disinfectant.

* * * * *

UNITED STATES PATENT AND TRADEMARK OFFICE
CERTIFICATE OF CORRECTION

| | | |
|---|---|---|
| PATENT NO. | : 8,617,482 B2 | Page 1 of 1 |
| APPLICATION NO. | : 12/999265 | |
| DATED | : December 31, 2013 | |
| INVENTOR(S) | : Ragnar Tryggvason et al. | |

It is certified that error appears in the above-identified patent and that said Letters Patent is hereby corrected as shown below:

In the Claims

Claim 3, col. 13, line 5, "at least One fluid" should read -- at least one fluid --.

Claim 17, col. 14, line 24, "wherein The disinfectant" should read -- wherein the disinfectant --.

Signed and Sealed this
Sixth Day of May, 2014

Michelle K. Lee
*Deputy Director of the United States Patent and Trademark Office*